United States Patent [19]

Dabi

[11] Patent Number: 4,508,854

[45] Date of Patent: Apr. 2, 1985

[54] QUATERNIZED CELLULAR POLYMERS FROM AMINE TERMINATED POLY(AMINOETHERS) AND POLYFUNCTIONAL EPOXIDES

[75] Inventor: Shmuel Dabi, Highland Park, N.J.

[73] Assignee: Personal Products Company, Milltown, N.J.

[21] Appl. No.: 604,708

[22] Filed: Apr. 27, 1984

[51] Int. Cl.[3] ............................................. C08J 9/08
[52] U.S. Cl. .................................. 521/178; 521/135; 525/523; 528/111
[58] Field of Search ................. 525/523; 528/111; 521/178, 135

[56] References Cited

U.S. PATENT DOCUMENTS

| | | | |
|---|---|---|---|
| 3,306,809 | 2/1967 | Williamson et al. | 528/111 |
| 3,316,185 | 4/1967 | Reinking | 528/111 |
| 3,380,881 | 4/1968 | Williamson et al. | 528/361 |
| 3,462,393 | 8/1969 | Legler | 528/111 |
| 3,645,969 | 2/1972 | Harvey | 528/407 |
| 4,423,166 | 12/1983 | Moriarity et al. | 528/111 |
| 4,423,170 | 12/1983 | Waddill | 528/111 |

FOREIGN PATENT DOCUMENTS 0030668  6/1981  European Pat. Off. ............ 521/178

OTHER PUBLICATIONS

Chem. Abstracts, vol. 95: 116530p, 1981.

*Primary Examiner*—Morton Foelak
*Attorney, Agent, or Firm*—Jason Lipow

[57] ABSTRACT

An absorbent cellular polymeric material is provided which exhibits enhanced water retentivity and may also exhibit enhanced compressibility. Such a material is provided by foaming the reaction product of a poly(aminoether) and an epoxy resin and quaternizing the resulting reaction product with, for example, an acid. The foam is particularly usable in products for absorbing body fluids.

13 Claims, No Drawings

QUATERNIZED CELLULAR POLYMERS FROM AMINE TERMINATED POLY(AMINOETHERS) AND POLYFUNCTIONAL EPOXIDES

BACKGROUND OF THE INVENTION

This invention concerns providing cellular polymers suitable for use in products for absorbing body fluids such as for example, sanitary napkins, catamenial tampons, diapers, bandages, surgical dressings and the like. Such materials, commonly referred to as foams have already been considered for use in such products and various polymers and processes have been suggested as suitable including, for example, polyurethane foams, polyester foams and cellulose foams.

While these foams, in the main, have been capable of absorbing body fluids to varying degrees, their properties having fallen short of those preferred for products such as diapers, sanitary napkins and the like. In general these prior art foams lack the characteristics of efficient wicking and good liquid retention. In many cases the foams are either not compressible or if compressible, not readily expandable when wetted.

A major forward step in the art of providing foams for use in body fluid absorbing products is disclosed in my copending U.S. patent application Ser. No. 485,782, filed on Apr. 18, 1983 for Resilient Cellular Polymers from Amine Terminated Poly(oxyalkylene) and Polyfunctional Epoxides, the specification of which is incorporated herein by reference. As taught therein, a usable foam may be prepared by foaming the reaction product of amine terminated poly(oxyalkylene) and polyfunctional epoxides, provided that the poly(oxyalkylene) component comprises poly(ethylene oxide) and poly(propylene oxide) wherein the ratio of ethylene oxide groups to propylene oxide groups are within a critical range. The resulting foam is absorbent, exhibits good wicking properties, and is highly resilient.

While this latter described foam is useful for many purposes, improvement is still desired. Specifically, it is desirable to improve the water retention properties of foam when under the influence of pressure. This property is of great importance in such body fluid absorbent products as diapers and napkins which are worn by the user and, after being wetted, are subject to pressure by the body movements of the wearer. Further, while in some applications, the dry resiliency of these foams are advantageous as they provide a measure of comfort to the user, in other applications, dry resiliency is disadvantageous. For example, particularly in the case of sanitary napkins, panty shields, catamenial tampons, or the like, it is desirable to produce as thin a product as is possible. In this instance the preferred absorbent material would be one which is highly compressible in the dry state, i.e., capable of being compressed into a thin sheet or small cylinder, as for catamenial tampons, and then has the characteristic of expanding upon wetting, thereby providing the intercellular void volume for taking up the body fluid. The prior foams lack these properties. Further still, the latter described foams are the products of a rather limited class of polymers and because of economic or availability considerations, it is desirable to expand the class of suitable polymers for use in providing usable foam.

Accordingly, there is a need for improvement in providing foams for use in absorbing fluids and particularly for absorbing body fluids.

SUMMARY OF THE INVENTION

In accordance with this invention, an absorbent cellular polymeric material, i.e., foam, is provided which exhibits enhanced water retentivity and in a specific embodiment, exhibits enhanced compressibility.

Specifically, it has been discovered that such a material may be provided by foaming the reaction product of a poly(amino ether) and an epoxy resin and quaternizing the resulting reaction product as with an acid. The poly(amino ether) should have the empirical formula:

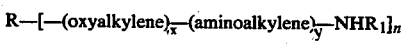

wherein R is selected from the group consisting of (a) an aminoalkylene group having a valence of n and 1 to 6 carbon atoms or (b) the residue of a polyhydric alcohol after removal of n alcoholic hydroxyl groups and having from 1 to 6 carbon atoms; $R_1$ is selected from the group consisting of H or alkyl having from 1 to 4 carbon atoms; x and y are numbers ranging from 0 to 100 with the sum of x or y being equal to at least 2; and n having a value of from 1 to 3.

A preferred group of poly(amino ethers) within this class have the general formula

wherein R, $R_1$ and n have the same meaning as above and x varies from integers of 2 to 100. The oxyalkylene units may be mixtures of oxyalkylenes, each having from 2 to 4 carbon atoms.

A wide variety of epoxy monomers and polymers are suitable for use and are well known in the art. It is preferred that the epoxy resin be supplied to the reaction mix such that in the aggregate, the reaction mixture comprises from about 1.0 to about 3.0 epoxy group per amine group of the poly(amino ether) and still more preferably from about 1.2 to about 2.0 epoxy group per amine group. The epoxy resin of choice are the di- and polyglycidyl ethers of bisphenols, the bisphenols having the formula:

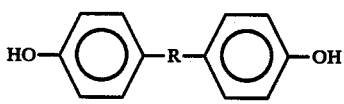

wherein R is a bivalent radical containing 1 to 8 atoms of C, O, S, and/or N and more preferably, an alkyl or alkylene group containing 1 to 8 carbon atoms or still more preferably 1 to 6 carbon atoms.

The foam is prepared by combining the reactants at room temperature or more preferably at an elevated temperature to form an intermediate reaction product which is preferably at the point in the reaction just prior to gelation or gel point. A blowing agent is then introduced to create the cells of the foam. A preferable blowing agent is one which releases carbon dioxide or nitrogen gas upon activation.

The resulting reaction product has amine functions and, in accordance with the teachings of this invention such amine functions are quaternized to the degree sufficient to increase the water retention properties of the cellular polymeric material. It has been discovered that a significant increase in retentivity is realized when at least 10% of the amine functions of the reaction product have been quaternized and preferably when at least 50% have been quaternized. Of course, all the amine functions may be quaternized with a concomitant improvement in retentivity.

The quaternizing of the amino group of the reaction product may be accomplished at any time after formation of the reaction product by the introduction or inclusion of quaternizing agents. Such agents are well known in the art and include, for example, organic and inorganic acids, and such compounds as dimethylsulfate and methyl iodide.

In a specific embodiment, the cellular, polymeric material of this invention, is provided with the property of compressibility. As used herein, the term "compressibility" means a cellular material, i.e, foam, which is capable of being deformed under pressure in the dry state and will remain deformed until subsequently wetted whereupon the material will greatly expand. As has been described above, this property is particularly useful in the manufacture of thin body fluid absorbent products such as sanitary napkins, panty shields, and catamenial tampons. In accordance with this aspect of the invention, the epoxy resin employed to react with the poly(amino ether) is one subjected to a ring opening reaction with an acid so that a portion of the epoxy rings undergo the following reaction, with, for example, acetic acid:

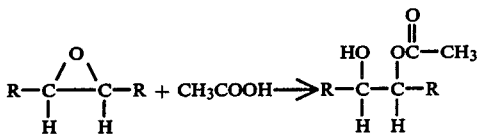

The ring opening reaction may be employed prior to reacting the epoxy resin with the poly(amino ether) but preferably, acid may be added directly to the reaction mixture of epoxy resin and poly(amino ether) whereby the acid will compete with the amino groups for reaction with the epoxy groups. The degree of ring opening can be controlled by varying such factor as the acid concentration employed or the strength of the acid chosen. A high acid concentration will favor the ring opening reaction over the competing reaction of the epoxy ring with the amino group of the poly(amino ether). Similarly, employment of a stronger acid will favor such ring opening reaction. In general, the greater the degree of ring opening, the more compressible the cellular polymeric material will be.

DETAILED DESCRIPTION OF THE INVENTION

The invention provides a foam which is the reaction product of poly(amino ether) and epoxy resin, said reaction product having quaternized amine groups.

The poly(amino ether) may be in the form of mixtures of poly(amino ethers), copolymers of amine ethers such as random copolymers or block copolymers or even mixtures of the above.

In general, the poly(amino ethers) have the formula:

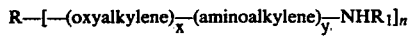

wherein R is selected from the group consisting of (a) an aminoalkylene group having a valence of n and 1 to 6 carbon atoms or (b) the residue of a polyhydric alcohol after removal of n alcoholic hydroxyl groups and having from 1 to 6 carbon atoms; $R_1$ is selected from the group consisting of H or alkyl having from 1 to 4 carbon atoms; x and y are numbers ranging from 0 to 100 with the sum of x or y being equal to at least 2; and n having a value of from 1 to 3.

A preferred group of poly(amino ethers) within this class have the general formula

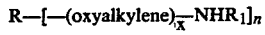

wherein R, $R_1$ and n have the same meaning as above and x varies from 2 to 100. The oxyalkylene units may be mixtures of oxyalkylenes, each having from 1 to 4 carbon atoms.

Examples of this preferred group of poly(amino ethers) are the amine terminated poly(alkylene oxides) described in connection with my above-referenced co-pending patent application and available from the Texaco Chemical Company of Bellaire, Tex., under the trademark "Jeffamine" compounds. Within this series of compounds is, for example, a series of Jeffamine compounds designated by Texaco as Jeffamine ED compounds and having the structure:

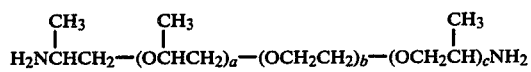

These block copolymers are derived from polypropylene oxide capped polyethylene glycol and are available from Texaco as compounds wherein the a, b, and c values are in the following ratios:

| Jeffamine Compound | Approximate Value of | |
| --- | --- | --- |
| | b | a + b |
| ED-600 | 13.5 | 3.5 |
| ED-900 | 20.5 | 3.5 |
| ED-2001 | 45.5 | 3.5 |

Suitable foams have also been prepared by combining these amine terminated poly(alkylene oxides) with a polyoxypropylene amine sold by the Texaco Chemical Company under the name JEFFAMINE T-403 and having the following chemical structure:

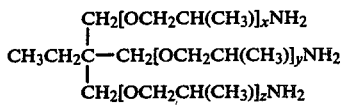

wherein the sum of x+y+z is equal to about 8.3.

Within the broad class of poly(amino ethers) described above are those having the general formula

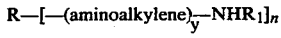

wherein R, $R_1$, y, and n have the meaning described above and y is equal to from 2 to 100. The aminoalkylene groups may be mixtures of aminoalkylenes having from 1 to 4 carbon atoms. An example of such a poly(amino alkylene) is polyethyleneimine.

Many epoxy monomer and polymer are suitable for use. Such epoxy resins have already been suggested for use in providing hydrophobic foams from amine-terminated liquid polymers and are described in a European patent application, No. 80107479.0 of the B. F. Goodrich Company claiming priority to a U.S. application filed on Dec. 3, 1979 and published June 24, 1981.

The epoxy resins described therein and usable in producing the foams of this invention contain at least an average of about 1.7 epoxy groups per molecule, more preferably from about 1.7 to about 4 epoxy groups per molecule, and even more preferably from about 1.7 to about 2.3, epoxy groups per molecule. The epoxy resins may be liquids or low-melting solids but are preferably liquids having a bulk viscosity from about 200 centipoises to about 2,000,000 centipoises, measured using a Brookfield RVT viscometer at 25° C. The epoxy resins can have an epoxy equivalent weight, i.e., gram molecular weight per epoxy group, from about 70 to about 6,000, more preferably from about 70 to about 2,000. Examples of suitable polyglycidyl esters of polycarboxylic acids include the diglycidyl ester of linoleic dimer acid, the triglycidyl ester of linoleic trimer acid, and the like. Suitable glycidyl ether resins include polyalkyl glycidyl ether, and diglycidyl ether of chlorendic diol, the diglycidyl ether of dioxanediol, and diglycidyl ether of endomethylene cyclohexanediol, epoxy novolac resins, alkanediol diglycidyl ethers, alkanetriol triglycidyl ethers, and the like.

More preferred glycidyl ether resins include alkanediol diglycidyl ethers having the formula

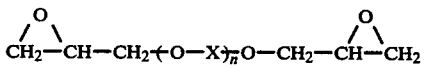

wherein X is an alkylene or alkylidene group containing from 1 to 10 carbon atoms, more preferably from 2 to 6 carbon atoms, and n is from 1 to 25, more preferably from 1 to 15. Suitable alkanediol diglycidyl ethers include ethylene glycol diglycidyl ether, propylene glycol diglycidyl ether, butanediol diglycidyl ether, and the like. Other more preferred glycidyl ether resins include alkanetriol triglycidyl ethers wherein the alkane group contains from 2 to 10 carbon atoms, more preferably from 3 to 6 carbon atoms, such as glyceryl triglycidyl ether, the triglycidyl ether of trimethylolpropane, and the like.

This class of glycidyl ether resins produces a foam, in accordance with the teachings of this invention, which is soft, absorbent and resilient. Unfortunately, this group reacts disadvantageously slowly. A most preferred class of glycidyl ether resins is the di- and polyglycidyl ethers of bisphenols, the bisphenols having the formula

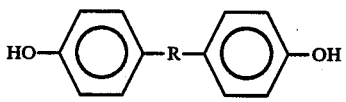

wherein R is a bivalent radical containing 1 to 8 atoms of C, O, S and/or N, more preferably an alkylene or alkylidene groups containing 1 to 8 carbon atoms, and even more preferably an alkylene or alkylidene groups containing 1 to 6 carbon atoms. Examples of suitable bisphenols include methylene bisphenol, isopropylidene bisphenol, butylidene bisphenol, octylidene bisphenol, bisphenol sulfide, bisphenol ether, bisphenol amine, and the like. Excellent results were obtained using isopropylidene bisphenol. The latter epoxy resin not only produces a foam with the desired properties but also is quite reactive and is most suitable for use in connection with the teachings of this invention.

The proportions of epoxy resin to poly(amino ether) in the reaction mixture may vary over a substantial range. Preferably, the ratio of active epoxy groups to amine groups may range from about 1 to about 3. More preferably this ratio varies from about 1.2 to about 2.0 epoxy groups per amine group.

The production of the foams of this invention is best carried out using a two step process consisting of first performing an intermediate reaction step and then foaming the reaction mixture as polymerization continues.

The intermediate reaction step is carried out by first mixing the epoxy resin and poly(amino ether) in the proportions taught herein. The reaction mixture is then heated and maintained at a reaction temperature which may range from about 25° C. to about 130° C. In practice, temperatures much below 50° C. will require a disadvantageously long reaction time whereas temperatures above 110° C. will result in a reaction time which is too short and hence difficult to control. Accordingly, a preferable temperature range is between about 50° C. and about 110° C. with a range of about 65° C. to about 110° C. being most preferable. As the reaction proceeds and polymerization occurs between the epoxy resin and the poly(amino ether), the viscosity of the reaction mixture rises. The degree of intermediate reaction may be monitored and controlled by a continuous or incremental measurement of the reaction mixture viscosity. Alternatively, other properties could be measured which indicate the progress of the reaction e.g., density, refractive index, mechanical or electrical properties or the like.

Irrespective of what properties are used to measure the progress of the reaction, as the reaction proceeds, the mixture passes from the liquid state to that of a relatively inelastic solid. The transition state between liquid and solid is generally referred to as the gelation state and, ideally, it is just prior to this point in the reaction process that a blowing agent should be introduced to produce a stable foam having uniform cells. Too early an introduction of blowing agent results in the gas diffusing through the relatively liquid reaction mixture and hence failing to form stable cells. Too late an introduction will result in the now substantially solidified reaction mixture being too inelastic to allow the gas to form cells.

It has been discovered that advantageously a foaming agent introduced when the reaction mixture reaches a viscosity of from about 1000 cps. to about 12,000 cps (measured at 25° C.). Depending primarily on the temperature at which the reaction is run, typically such viscosity range can be reached in a time period of as short as 10 minutes or as long as two hours.

A wide variety of foaming agents may be employed. For example, certain compounds may be introduced which release gases upon heating. Examples of this type of foaming agent are azo bis(isobutyronitril) and benzene sulfonyl hydrazide which release nitrogen gas when heated.

A preferred method of foaming is to mix into the reaction mixture a compound or mixture of compounds such as sodium carbonate or sodium bicarbonate. Upon the addition of a suitable acid or acidic salt, these compounds react to release carbon dioxide gas to perform the foaming. Suitable acids or acid compounds may be for example, hydrochloric acid; phosphoric acid; organic acids such as acetic, lactic, citric, etc., sodium bisulfate; potasssium dihydrogen phosphate or the like.

The foaming agents may be added to the initial copolymerization reaction mixture when such mixture is at a temperature of from 30° C. to about 110° C. Preferably, to have a controlled release of carbon dioxide, for example, the reaction mixture should be at a temperature ranging from about 40° C. to about 80° C. Accordingly, it may be necessary to first reduce the temperature of the initial copolymerization reaction mix prior to adding the foaming agents. After foaming is initiated, the foaming is completed by heating, preferably in an oven for about five to about twenty minutes at an elevated temperature ranging from about 120° C. to about 140° C.

In accordance with the teachings of this invention the reaction product of the poly(amino ether) and the epoxy resin have amine functions which are quaternized, which quaternizing may take place at any time after the formation of the reaction product by the introduction or inclusion of quaternizing agents. Any inorganic or organic acid, preferably water soluble, may be employed. Such inorganic acids as for example, hydrochloric, sulfuric or phosphoric acid are suitable. Organic acids such as those having the general formula

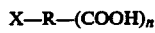

X—R—(COOH)$_n$ wherein X is selected from the group consisting of halogen, hydroxyl, amine, mercaptan, hydrogen; R is selected from the group consisting of aliphatic, aromatic or alicyclic hydrocarbons radicals; and n is an integer equal to one or more e.g., 1 to 3. Examples of such usable organic acids are acetic, lactic, citric, tartaric, succinic, adipic, chloroacetic, dimethylolpropionic, glycolic, glutaric, β-alanine, thioglycolic, polyacrylic, salicylic, aminobenzoic and others.

Non-acid agents also useful for quaternizing the finished foam of this invention are such agents as dimethylsulfate and methyl iodide.

In accordance with the simplest embodiment of this invention, the reaction product of the poly(amino ether) and the epoxy resin is treated with the quaternizing agent to quaternize the amino groups. The following example illustrates this embodiment.

EXAMPLE 1

The following components are thoroughly mixed and heated at 120° C. for 15 minutes:

| Component | Parts (By Weight) |
|---|---|
| A diglycidyl ether of bisphenol A sold under the tradename EPON 828 by the Shell Oil Co. | 28.5 |
| JEFFAMINE T-403 (identified above) | 3.7 |
| JEFFAMINE ED-900 (identified above) | 58.5 |

The mixture is cooled to 100° C. and 3.6 parts by weight of sodium carbonate is then dispersed into the prepolymer by means of a high shear mixer. A quantity of lactic acid, in an 85% by weight acid aqueous solution is stirred into the mixture, such acid quantity (4.5 parts by weight) being sufficient only to neutralize the sodium bicarbonate i.e., there is essentially no ring opening reaction. The mixture, which turns creamy immediately, is poured into a paper mold and allowed to cure for fifteen minutes at 140° C. The resulting foam is then quaternized by first neutralizing 15.8 parts by weight of an 85% by weight lactic acid aqueous solution with 9.4 parts by weight of a 27% by weight ammonia solution. The foam is soaked in the neutralized solution until it is completely absorbed. The foam is then initially dried in a microwave oven, followed by further drying in a hot air oven. It should be noted that the quaternization is accomplished by having the foam first absorb a neutralized solution. Subsequently, during the heating step, the ammonia is volatalized whereby the resulting lactic acid quarternizes the amino groups of the foam, such quaternizing being substantially uniform throughout the body of the foam. If instead, non-neutralized lactic acid is applied to the body of the foam, the portion of the foam to first contact the lactic acid would be quaternized to a relatively complete extent and the remainder of the foam would be quaternized to a lesser extent or even not at all. The result would be a body of foam having non-uniform absorption properties.

It can be seen, therefore, that the application of neutralized solution followed by heating produces an uniformly absorbent foam which is generally preferred for purposes of utilizing the foam in body fluid absorbent products. On the other hand, should it be desired to produce a foam having non-uniform properties, e.g., highly retentive on one side only, this may be accomplished by applying an acid solution to one side only. Means, such as those commonly used in the process of suction bonding of nonwoven fabrics, may be employed for controlling the distribution of quaternizing agent in the foam.

The above method of quaternizing the finished, foamed reaction product of the poly(amino ether) and the epoxy resin produces a highly absorbent, retentive foam which is highly resilient in both the wet and dry state. Such a product is usable in a variety of body fluid absorbing products. When compressed in the dry state, the foam will recover easily and hence does not have the property of compressibility, as the term is used herein. In a specific embodiment of this invention, the foam is endowed with the property of compressibility by having the epoxy resin undergo a ring opening reaction with acid prior or during the reaction of the epoxy resin with the poly(amino ether). The following example illustrates this embodiment.

EXAMPLE 2

The following components are thoroughly mixed and heated at 115° C. for 10 minutes:

| Component | Part (By Weight) |
|---|---|
| EPON 828 | 17.1 |
| JEFFAMINE T-403 | 2.0 |
| JEFFAMINE ED-600 | 14.0 |
| JEFFAMINE ED-900 | 5.1 |
| Citric Acid | 5.0 |

One gram of azo-bis-isobutyronitrile is thoroughly combined with the reaction mixture which is then poured into a preheated paper mold and allowed to rise in an oven heated to 140° C. The final foam was stiff and compressible in the dry state.

EXAMPLE 3 AND 4

The effect of the quaternizing of the amino groups of the reaction product of the poly(amino ether) and epoxy resin are illustrated by these examples. The poly(amino ether) and the epoxy resin as set out in the table below are thoroughly mixed and heated at 120° C. for 15 minutes. The mixture is cooled to 100° C. and the sodium bicarbonate is then dispersed into the prepolymer by means of a high shear mixer. The neutralizing lactic acid, in the form of an 85% by weight acid aqueous solution is stirred into the mixture, such acid being sufficient only to neutralizing the sodium bicarbonate. The mixture which turns creamy, is poured into a paper mold and allowed to air for fifteen minutes at 140° C. The resulting foam is then quarternized with the remaining lactic acid using the method illustrated in Example 1 above.

The foams obtained are tested for fluid retention by weighing a dry sample measuring 1 inch by 1 inch by ¼ inch and then immersing the sample in deionized [?] water for one minute. The wet foam is removed and placed on a dry paper towel. Pressure, in the form of a weight and as is set out in the table below, is applied to the wet foam and the towel is allowed to absorb the water flowing from the foam. The foam is repeatedly placed on another paper towel and pressure applied until no more water flows from the foam. The foam is then weighed and the water retained is calculated and reported in the table below.

TABLE 1

|  | Example 3 | Example 4 |
|---|---|---|
| Component (parts by weight) | | |
| EPON 828 | 9.5 | 9.3 |
| T-403 | 1.2 | 1.2 |
| ED-600 | 12.8 | 12.8 |
| SODIUM BICARBONATE | 1.0 | 1.0 |
| LACTIC ACID (NEUTRALIZING) | 1.0 | 1.0 |
| LACTIC ACID (QUARTERNIZING) | — | 4.3 |
| Water Retention (g/g) | | |
| @ 0.022 ATMOS | 2.24 | 6.5 |
| @ 0.033 ATMOS | 1.84 | 5.6 |

As Table 1 illustrates, the quarternized foam, Example 4, retains substantially greater qualities of water than the unquarternized foam, Example 3.

EXAMPLES 5 AND 6

The procedure for producing quarternized and unquarternized foam as described in Example 3 and 4 is carried out for foams made from the composition set out below in Table 2.

TABLE 2

|  | EXAMPLE 5 | EXAMPLE 6 |
|---|---|---|
| COMPONENT (PARTS BY WEIGHT) | | |
| EPON 828 | 9.5 | 9.5 |
| T-403 | 1.2 | 1.2 |
| ED-900 | 19.5 | 19.5 |
| SODIUM BICARBONATE | 1.0 | 1.0 |
| LACTIC ACID (NEUTRALIZING) | 1.0 | — |
| Dimethylol propionic ACID (QUATERNIZING) | | 6.7 |
| WATER RETENTION (g/g) | | |
| @ 0.022 ATMOS | 2.8 | 7.35 |
| @ 0.033 ATMOS | — | 6.3 |

Again, it can be seen that the quarternized sample, Example 6, retained substantially more water than the unquaternized sample, Example 5.

The following examples illustrate the effect of acid treatment and preparation method on the final properties of the foam.

EXAMPLE 7

The following components are thoroughly mixed and then heated at 110° C. for 45 minutes to form a viscous resin.

| COMPONENT | PARTS BY WEIGHT |
|---|---|
| EPON 828 | 50.4 |
| ED-2001 | 13.2 |
| ED-600 | 6.0 |

Two parts by weight of a blowing agent, 4,4-oxy-bisbenzene sulfurhydroxide (sold by the Olin Chemical Corporation under the trademark Nitropore OBSH) is dissolved in the viscous resin. A solution of 27 parts by weight ED-600, 2.0 parts by weight water and 1.0 parts by weight of a surfactant (ethylene oxide/propylene oxide block copolymer, sold by BASF as L-62) is heated to 100° C. and added to the viscous resin with vigorous stirring. The mixture turns creamy and starts to rise. Curing is completed by heating in an oven at 130° C. for 10 minutes.

EXAMPLE 8

The procedure of Example 7 is followed, with the exception that 8 parts by weight of citric acid is added along with the blowing agent.

EXAMPLE 9

The procedure of Example 7 is followed and the resulting foam is then treated by first neutralizing 8 parts by weight of citric acid with 7.2 parts by weight of a 27%, by weight, ammonia solution. This neutralized solution is diluted to 10% parts by weight and the foam is soaked in the diluted solution until the solution is completely absorbed and then dried in a microwave and hot air oven.

In summary, Example 7 represents a foam which has not been quaternized or subjected to a ring opening reaction as taught herein. Example 8, wherein citric acid is added to the reaction mixture, is subjected to both quaternization and ring opening. Finally, Example 9 wherein citric acid is introduced after the foam is formed, is subjected to quaternization only. The Table 3 below, illustrates the varying properties resulting from these different treatments.

TABLE 3

| EXAMPLE | WATER RETENTION (g/g) | | WET EXPANSION % | DRY RESILIENCY (seconds) TIME TO RECOVER |
|---|---|---|---|---|
| | 0.022 ATMOS | 0.033 | | |
| 7 | 3.8 | 2.8 | 15 | 1 |
| 8 | 4.2 | 3.4 | 180 | 3600 |
| 9 | 6.5 | 4.6 | 55 | 3 |

As can be seen from the above Table 3, Example 7 wherein the foam was neither quaternized nor subjected to ring opening, exhibited the poorest values for water retention, wet expansion and dry resiliency. Wet expansion is the volume of the foam [saturated] with water, based on the dry volume. Dry resiliency is the time required for dry foam to recover from an 80% deformation imposed at room temperature. Example 8, subjected to both quaternization and ring opening showed substantial improvement in retention and dramatic improvement in compressibility i.e., slow recovery.

Example 9, wherein the same quantity of acid was employed after the foam was formed showed the greatest increase in retention and essentially no improvement in compressibility. As contrasted with the method of Example 8, the acid provided all went toward quaternizing the amine groups of the reaction product and did not compete with the poly(amino ether) in reaction with the epoxy groups. Accordingly, a greater proportion of the amine group were quaternized with the concommitant result of enhanced retention. On the other hand, essentially no ring opening occurred and hence no significant improvement in compressibility.

What is claimed is:

1. An absorbent cellular polymeric material comprising the reaction product of a poly(amino ether) and an epoxy resin, said reaction product having quaternized amine groups.

2. The absorbent cellular polymeric material of claim 1 wherein the poly(amino ether) has the empirical formula:

wherein
R is selected from the group consisting of:
(a) an aminoalkylene group having a valence of n and 1 to 6 carbon atoms or;
(b) the residue of a polyhydric alcohol after removal of n alcoholic hydroxyl group and having from 1 to 6 atoms;
$R_1$ is selected from the group consisting of H or alkyl having from 1 to 4 carbon atoms;
x and y are numbers ranging from 0 to 100 with the sum of x or y being equal to at least 2; and
n has a value of from 1 to 3.

3. The absorbent cellular polymeric material of claim 1 wherein the poly(amino ether) has the formula:

wherein
R is selected from the group consisting of:
(a) an aminoalkylene group having a valence of n and 1 to 6 carbon atoms; or
(b) the residue of a polyhydric alcohol after removal of n alcoholic hydroxyl groups and having from 1 to 6 carbon atoms;
$R_1$ is selected from the group consisting of H or alkyl having from 1 to 4 carbon atoms;
x is from 2 to 100; and
n has a value of from 1 to 3.

4. The absorbent cellular polymeric material of claim 1 wherein said poly(amino ether) comprises a compound having the empirical formula

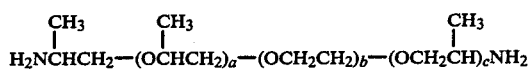

wherein b has an empirical value of from about 10 to about 50 and the sum of a and c has an empirical value of from about 1 to about 5.

5. The cellular polymeric material of claim 1 wherein said amine terminated poly(alkylene oxide) comprises a compound having the empirical formula:

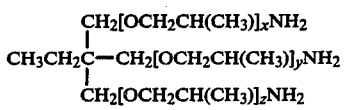

wherein the sum of x+y+z is equal to from about 7 to about 10.

6. The cellular polymeric material of claim 1 wherein said epoxy resin has an average ratio of epoxy groups per molecule of epoxy resin of at least 1.7.

7. The cellular polymeric material of claim 6 wherein said epoxy resin has an average ratio of epoxy groups per molecule of epoxy resin ranging from about 1.7 to about 4.

8. The cellular polymeric material of claim 1 wherein said epoxy resin comprises a polyglycidyl ester of a polycarboxylic acid.

9. The cellular polymeric material of claim 1 wherein said epoxy resin comprises a glycidyl ether resin.

10. The cellular polymeric material of claim 9 where said epoxy resin comprises an alkanediol diglycidyl ether having the formula:

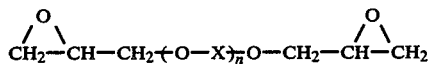

wherein x is selected from the group comprising alkylene or alkylidene groups containing from 1 to 10 carbon atoms, and n has a value of from 1 to 25.

11. The cellular polymeric material of claim 9 wherein said epoxy resin is selected from the group consisting of di- and polyglycidly ethers of bisphenols, said bisphenols having the formula:

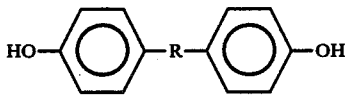

wherein R is a bivalent radical containing 1 to 8 atoms selected from the group consisting of C, O, S, or N.

12. The cellular polymeric material of claim 11 wherein R is selected from the group consisting of alkylene or alkylidene radicals containing from about 1 to about 8 carbon atoms.

13. The cellular polymeric material of claim 12 wherein said epoxy resin comprises isopropylidene bisphenol.

* * * * *